(12) United States Patent
Konstantinov et al.

(10) Patent No.: US 7,674,885 B2
(45) Date of Patent: Mar. 9, 2010

(54) PROCESS FOR CONCENTRATION OF MACROMOLECULES

(75) Inventors: Konstantin Konstantinov, Walnut Creek, CA (US); Huong Nguyen, San Francisco, CA (US); Jens H. Vogel, Richmond, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 618 days.

(21) Appl. No.: 10/532,998

(22) PCT Filed: Nov. 1, 2003

(86) PCT No.: PCT/US03/34522

§ 371 (c)(1),
(2), (4) Date: Nov. 10, 2005

(87) PCT Pub. No.: WO2004/042012

PCT Pub. Date: May 21, 2004

(65) Prior Publication Data

US 2006/0149042 A1 Jul. 6, 2006

Related U.S. Application Data

(60) Provisional application No. 60/422,999, filed on Nov. 1, 2002.

(51) Int. Cl.
*A23J 1/00* (2006.01)
*C07K 1/00* (2006.01)

(52) U.S. Cl. .................. 530/414; 530/418; 530/421

(58) Field of Classification Search .................. None
See application file for complete search history.

(56) References Cited

U.S. PATENT DOCUMENTS

| | | | |
|---|---|---|---|
| 4,960,702 A | 10/1990 | Rice et al. | |
| 5,417,970 A | 5/1995 | Roskam et al. | |
| 5,552,303 A | 9/1996 | Grabstein et al. | |
| 5,814,478 A | 9/1998 | Valenzuela et al. | |
| 6,087,148 A * | 7/2000 | Rancke-Madsen et al. | .. 435/209 |
| 6,103,502 A | 8/2000 | Möller et al. | |
| 6,143,331 A * | 11/2000 | Koch et al. | .................. 424/580 |

FOREIGN PATENT DOCUMENTS

WO    WO-9712915    4/1997

OTHER PUBLICATIONS

Palomares et al. Evidence of Pluronic F-68 direct interaction with insect cells: impact on shear protection, recombinant protein, and baculovirus production. Enzymes and Microbial Technology, Mar. 2000, vol. 26, No. 5-6, pp. 324-331.*
Nemeth et al. Antifoaming action of polyoxyethylene-polyoxypropylenepolyoxyethylene-type triblock copolymers on BSA foams. Colloids and Surfaces A: Physiochemical and Engineering Aspects, 1997, 127: 151-162.*
Schulz, C. et al., "Influence of Pluronic F-68 on the Ultrafiltration of Cell Culture Supernatants" in Carrondo et al. (eds.), Animal Cell Technology, From Vaccines to Genetic Medicine, 1997, Kluwer Acacemic Publishers.

* cited by examiner

*Primary Examiner*—Suzanne M. Noakes
(74) *Attorney, Agent, or Firm*—Connolly Bove Lodge & Hutz, LLP

(57) ABSTRACT

The invention provides methods for concentrating a macromolecule from a solution comprising the macromolecule and an organic polymer by first subjecting the solution to ultrafiltration to produce a first retentate solution, then adjusting the conductivity of the first retentate solution such that any protein precipitation induced by the organic polymer is essentially prevented to produce a second retentate solution, and then subjecting the second retentate solution to ultrafiltration. In a preferred embodiment, the conductivity is adjusted by diafiltration against water, suitable diluent or buffer.

Preferably, the invention pertains to the concentration of solutions of native or recombinant proteins. The invention further pertains preferably to methods for the concentration of cell culture supernatant comprising a product protein and organic polymers of the PLURONIC family of nonionic block co-polymers, and more preferably comprising PLURONIC F-68 nonionic block co-polymer.

11 Claims, 18 Drawing Sheets

PROCESS FOR CONCENTRATION OF MACROMOLECULES

This application is a national application (under 35 U.S.C. 371) of PCT/US2003/034522 filed Nov. 1, 2003 which claims priority to U.S. App. Ser. No. 60/422,999, filed Nov. 1, 2002, which is hereby incorporated by reference herein in its entirety.

BACKGROUND OF THE INVENTION

1. Field of the Invention

The present invention relates generally to the concentration of solutions of macromolecules such as proteins. In one embodiment, the inventive process involves the ultrafiltration of a solution comprising macromolecules and co-concentrating organic polymer, then a diafiltration to reduce conductivity, and then a second ultrafiltration to concentrate the macromolecule without significant loss of yield due to precipitation.

2. Description of Related Art

Protein production involves the creation of large volumes of comparatively dilute protein solution. It is preferred to concentrate the protein after fermentation to facilitate further steps, such as freezing, bulk storage and thawing and downstream purification. However, the ability to achieve optimal protein concentrations for products from solutions containing a co-concentrating organic polymer, such as is found in many cell culture supernatant solutions produced from mammalian cell culture harvest, has proved to be limited in the past due to increased precipitation (and thus loss) of the product molecules as concentration using ultrafiltration increases. For example, excessive precipitation has prevented concentration by ultrafiltration of more than 10-20 fold over the protein concentration in the initial cell culture supernatant.

The isolation, or primary recovery, process forms the interface between fermentation and downstream purification, and is often critical both in terms of production capacity and process economics. The main goal of the isolation process is to obtain the protein product in concentrated, particle-free solution, allowing further processing and downstream purification to be performed.

Ultrafiltration (UF) is an efficient technology for the concentration of protein solutions, and is frequently used as an important step in the isolation of proteins from cell culture supernatant. In particular, ultrafiltration is used in both batch and perfusion cell fermentation processes. Because continuous perfusion processes produce large volumes of comparatively dilute protein product, high concentration factors are desirable to facilitate downstream processes. A major limitation of conventional cell culture based protein manufacturing processes is the attainable concentration factor of protein isolation. In most cases, concentration factors of only 10-20 fold are reached using ultrafiltration during the isolation process. Attempts to increase concentration have resulted in increasing filterability problems and product losses due to precipitation. The nature and cause of the precipitation are generally unknown. Significantly higher concentration in the UF step is typically not easily attainable due to further increased precipitation. This can slow subsequent process steps because very large volumes have to be processed. This is especially true for continuous perfusion processes due to the comparatively low product titer and high volumetric throughput compared to batch fermentation.

Cell culture supernatants consist of a broad spectrum of compounds. These include supplements of the cell culture medium such as nonionic block copolymers, particularly the PLURONIC family of nonionic block copolymers sold by BASF, and silicon oil, and compounds that are secreted from cells or released after cell lysis (e.g., proteins, lipids). The nonionic block copolymer PLURONIC F-68 is usually required as a supplement in cell culture media to protect mammalian cells.

In a preferred embodiment, the present invention is directed to a process to increase the concentration of cell culture supernatant greatly without significant loss of product macromolecule yield or filterability problems. Applicants discovered surprisingly that a cell culture supernatant comprising the product macromolecules and an organic polymer that co-concentrates with the product macromolecules during ultrafiltration, such as a PLURONIC nonionic block copolymer, can be greatly concentrated with higher yields than any reported process of which the Applicants are aware by first subjecting the supernatant to an initial ultrafiltration, then adjusting the conductivity of the retentate, such as by diafiltration with water for injection (WFI), diluent or buffer, and then subjecting the solution to a second ultrafiltration.

BRIEF SUMMARY OF THE INVENTION

In connection with the present invention, there are provided methods for concentrating a macromolecule from an aqueous starting solution having solution components. The solution components comprise the macromolecule and an organic polymer. The macromolecule is concentrated by first subjecting the starting solution to ultrafiltration to concentrate the macromolecule such that a first retentate solution is produced, then adjusting the conductivity of the first retentate solution such that precipitation of the solution components induced by the organic polymer is substantially prevented or substantially reversed to produce a second retentate solution, and then subjecting the second retentate solution to ultrafiltration to further concentrate the macromolecule such that a concentrated solution is produced. In a preferred embodiment, the conductivity is adjusted by diafiltration against water, suitable diluent or buffer.

Preferably, the invention pertains to the concentration of aqueous solutions of native or recombinant proteins. The starting solution preferably comprises mammalian or insect cell culture supernatant. The invention further pertains preferably to methods for the concentration of cell culture supernatant comprising a product protein and organic polymers of the PLURONIC family of block co-polymers, and more preferably comprising PLURONIC F-68 nonionic block co-polymer. The invention can also be practiced using cell culture supernatants containing other organic polymers such as polyethylenglycols or antifoam compounds. The present methods produce solutions of proteins having high concentration factors (i.e. from 20 fold to 100 fold or higher, preferably from 75 fold to 100 fold or higher).

The present invention is further directed to products, compositions, and intermediates. Applicants discovered that during ultrafiltration, co-concentrated organic polymers such as PLURONIC F-68 nonionic block copolymer induce precipitation of macromolecules. It was also discovered that such precipitation depends on the ionic strength of the solution. Thus, in accordance with the present invention, there is provided a method of concentration of a solution comprising macromolecules and organic polymer. The method comprises first concentrating the solution to produce a first retentate solution, adjusting the ionic strength of the first retentate solution using a suitable diluting agent such that any precipitation of solution components induced by the organic polymer is substantially prevented or substantially reduced to obtain a second retentate solution, and then concentrating the second retentate solution by at least 50 fold, preferably at least 100 fold, and still more preferably by more than 100 fold compared to the macromolecule concentration of the starting solution and obtaining yields of from 75-100% of the macromolecule, preferably at least 95.0%, more preferably at least 99.0%, and particularly preferably a yield percent of 99.5 or greater of the macromolecule. In a preferred embodiment, the organic polymer comprises a member of the PLURONIC family of nonionic block copolymers, and more preferably comprises the nonionic block copolymer PLURONIC F-68. Optional further process steps can be conducted. For example, the macromolecule product of the inventive method can be subjecting to freezing, thawing, and post-thaw filtrating of the refined product to increase the purity or to prepare a desirable therapeutic dosage.

In a particular embodiment, the present invention is directed to solving the problem of PLURONIC nonionic block copolymer-induced protein precipitation. In a first step, the cell culture supernatant is concentrated, preferably by ultrafiltration, to a concentration factor where product loss is minimal (for example 20 fold relative to the original concentration). Then, preferably using the same equipment, all or a portion of the concentrate obtained in the first step above is diafiltered against water (WFI) or another a suitable buffer to lower the conductivity to a point where PLURONIC nonionic block copolymer-induced product precipitation is substantially prevented, i.e. a conductivity of below 6 mS/cm, and more preferably from 0.5 to 5 mS/cm. As used herein, conductivity measurements are conducted at 22° C. unless described otherwise. Finally, the material is further concentrated to achieve high final concentration factors (e.g. 75-100× relative to the original concentration) with little or no product loss and with minimized bulk protein precipitation. All three steps can be performed in the same equipment. In this case, there is generally little or no increase in complexity and no new material or hardware qualification is necessary. The initial filtration step allows minimization of WFI or buffer consumption during the step of diafiltration. Because the additional volume that has to be filtered during the diafiltration step is therefore low (usually the additional volume required during diafiltration is less than 20%, often less then 15%), the overall process time is not significantly prolonged.

In another embodiment, the initial ultrafiltration step does not occur. Instead, the process comprises first adjusting the conductivity of an aqueous starting solution, the starting solution having solution components, which components comprise a macromolecule and an organic polymer such that precipitation of the solution components induced by the organic polymer is substantially prevented or substantially reversed, then subjecting the solution to ultrafiltration to concentrate it greater than 50 fold, preferably greater than 75 fold, more preferably greater than 100 fold over the initial starting concentration.

A process according to the present invention allows for a significant increase in concentration factor, i.e. from 20 fold to 100 fold and higher, while also improving product yield compared to a conventional process. The instant process provides process yields from 75% to 100%, preferably from 90%-100%, and in many cases, up to 95%, or even up to 99.5%, which, in prior art, can only be achieved for much lower concentration factors of less then 10 to 20 fold. Bulk protein precipitation is significantly reduced when a process according to the present invention is employed. For example, filterability for a 20 fold concentrate ranges from 6 to 10 ml (10 ml being the theoretical maximum) as measured using an Acrodisc syringe filter 25 ml manufactured by Pall Corporation having 2.8 square cm of filter area at 10 pounds of pressure. This is a significant improvement compared to 1 to 5 ml using prior art processes. Using a process according to the invention one achieves better filterability for 75 fold concentrate (6 ml on average) than for 20 fold concentrate using a conventional prior art process (approx. 3 ml on average; see, i.e., filterability data shown in FIG. 17).

The present invention is further directed to protein solutions obtained from mammalian cell culture produced by a continuous or semi-continuous perfusion process having a concentration of over 20 fold protein compared to the protein concentration in the initial supernatant, preferably at least 50 fold, particularly preferably of at least 75 fold, a concentration of organic polymer of at least 20 g/l and preferably at least 50 g/l, and a yield of at least 75%, more preferably at least 90%, and more preferably at least 99% measured based on the amount of protein produced from the mammalian cell culture. In addition, the present invention is directed to a protein solution obtained from mammalian cell culture supernatant, wherein the protein solution has a 20 fold concentration of the protein compared to the concentration in the supernatant and has a filterability of at least 5 ml, preferably at least 6 ml, as measured using the Acrodisc syringe filter system discussed supra.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out herein.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF PREFERRED EMBODIMENTS

Figure 1:
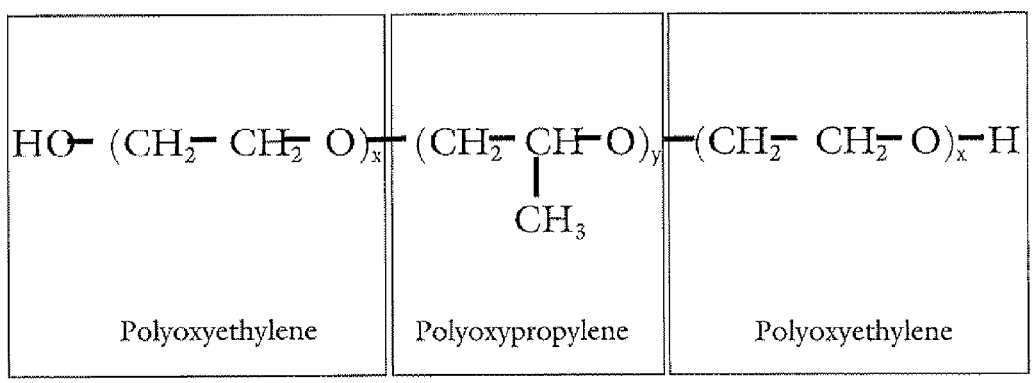
FIG. 1 shows the general structure of PLURONIC nonionic block copolymers.
Figure 2:
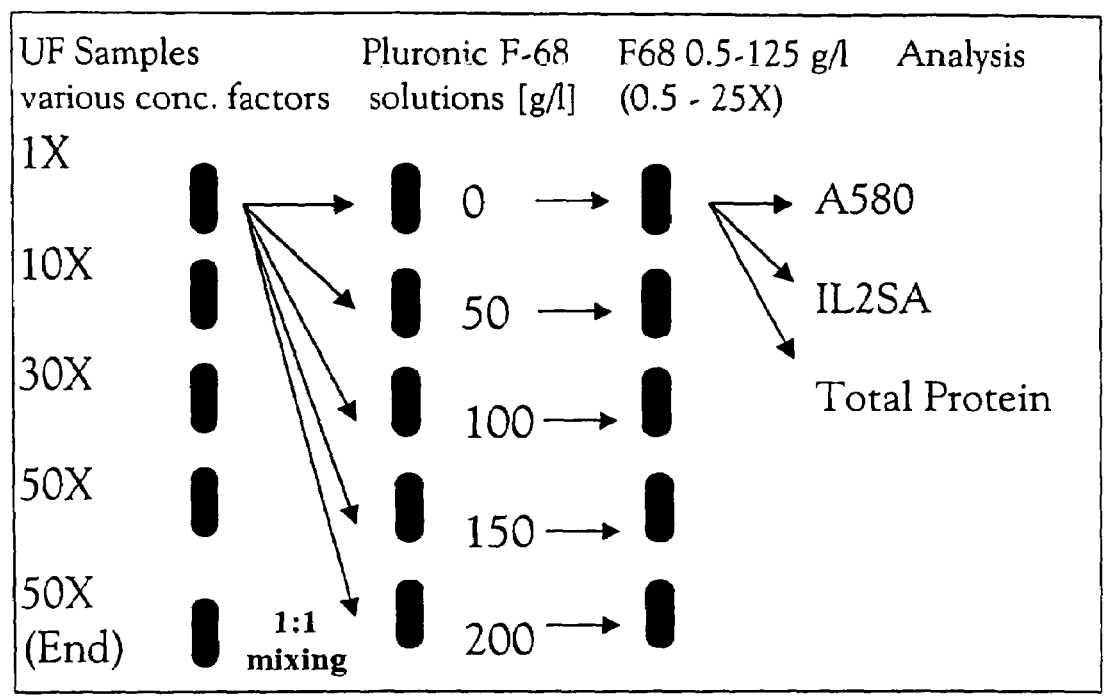
FIG. 2: Experimental set-up for PLURONIC F-68 nonionic block copolymer spiking experiments. Samples were taken from typical UF-concentration run (at 1×-50×; 50× (End) sample was taken from final UF concentrate drained from the system). PLURONIC P-68 nanionic block copolymer solutions were prepared in a standard cell culture medium (at 0-200 g/l). The result is a matrix of 25 solutions, with final concentration factors of 0.5-25 fold compared to supernatant and PLURONIC F-68 nonionic block copolymer concentrations between 0.5 and 125 g/l (assuming complete retention of PLURONIC F-68 nonionic block copolymer during UF and 1 g/l PLURONIC F-68 nonionic block copolymer concentration in the medium).

The present invention is advantageous for use with continuous or semi-continuous perfusion fermentation and batch fermentation processes. More preferably, the invention is directed to continuous or semi-continuous perfusion fermentation. As is well known in the art, producing proteins using continuous processes has certain advantages. The protein produced is generally of better quality due to the typically lower retention time in the bioreactor. Also proteins produced by continuous processes are less subject to degradation. In batch processes, there are typically higher protein concentrations in the fermentation supernatant, whereas with continuous processes, the protein produced is in more dilute solution.

Therefore, the present method is particularly beneficial for concentration of protein products obtained from continuous or semi-continuous perfusion processes, since comparatively more dilute protein solution has to be processed. Often in continuous perfusion the protein concentration is significantly less then 1 g/l and sometimes less then 0.1 g/l. High concentrations factors, preferably 100 fold and higher, are highly desirable to facilitate further downstream processing. In addition, the present invention can be used with batch-produced proteins if desired for any reason.

The present invention involves concentrating macromolecules from an aqueous solution having solution components. These solution components include the macromolecule and an organic polymer. The solution components also may include other compounds such as those commonly found in cell culture supernatant. For example, the components may include supplements of the cell culture medium such as silicon oil and anti-foam, and compounds that are secreted from cells or released after cell lysis (e.g., proteins and lipids such as are found in a host cell).

The present invention is particularly useful with solutions that are comprised of an organic polymer such as a member of the PLURONIC family of nonionic block copolymers, and more preferably comprised of PLURONIC F-68 nonionic block copolymer, which is an essential component of many cell culture media for protein manufacturing processes. Other organic polymers are also believed to co-concentrate with a desired macromolecule during ultrafiltration and lead to macromolecule or protein precipitation. Thus, the inventive methods apply to concentrate solutions comprising other co-concentrating organic polymers, such as polyethylene glycol ("PEG"), antifoam polymers and other polymers. In most instances, the protein precipitation is believed to occur as a result of the reduced dielectricity constant of the concentrated solution following ultrafiltration, as well as the increased competition for water molecules required for solvation of the co-concentrated organic polymers and macromolecules.

It is believed that the fundamental mechanism of precipitation of macromolecules induced by increased concentrations of an organic polymer such as, e.g., PLURONIC F-68 nonionic block copolymer, applies to solutions comprising other proteins and macromolecules beyond those discussed specifically in the examples. Therefore, the methods of the present invention can be employed with many different organic polymers and macromolecules. The solutions of macromolecules used in the inventive methods may be solutions of any macromolecules, preferably large biological macromolecules, and more preferably proteins. In one embodiment, a process according the present invention can be employed with the recombinant protein interleukin 2 selective agonist ("IL-2SA"). Other recombinant protein products that can be processed using techniques of the present invention include recombinant human Factor VIII sold by Bayer Corp. as Kogenate™, recombinant infliximab sold by Centocor, Inc. as Remicade™, recombinant abciximab sold by Johnson and Johnson as Reopro™, agalfidafe beta sold by Genzyme Inc. as Fabrazyme™, recombinant antihemophilic factor sold by Wyeth Ayerst as Refacto™ and recombinant antihemophilic factor sold by Baxter Inc. as Recombinate™ and any and all of their second and third generation versions, as well as many other protein products.

A main function of PLURONIC F-68 nonionic block copolymer is to protect the cells from potential damage caused by sparging (see e.g. Murhammer and Goochee, 1988; Murhammer and Goochee, 1990; Jordan et al., 1994), incorporated herein by reference) which is in turn necessary to ensure sufficient oxygen transfer within production scale bioreactors. Without the addition of protective substances like PLURONIC F-68 nonionic block copolymer, cells adhere to the gas-liquid interface (Chalmers and Bavarian, 1991). During rupture of the gas bubbles, the cells are subsequently subjected to very high shear stresses. Depending on the bubble diameter, maximum energy dissipation rates of up to $9.52*10^7$ $J*m^{-3}*s^{-1}$ have been reported, with smaller bubbles for more efficient aeration also creating higher shear stress (Boulton-Stone and Blake, 1993; Garcia-Briones et al., 1994). In comparison, energy dissipation rates in the order of $10^4$-$10^7$ $J*m^{-3}*s^{-1}$ are known to cause cell death in well-defined flow fields (e.g. Schurch et al., 1988, Augenstein et al., 1971).

PLURONIC F-68 nonionic block copolymer protects cells from being subjected to this high shear stress by preventing cell adhesion to the air-liquid interface (Garcia-Briones and Chalmers, 1992), which appears to be a result of the lowering of the dynamic surface tension by PLURONIC F-68 nonionic block copolymer (Michaels et at, 1995b). Moreover, PLURONIC F-68 nonionic block copolymer has been shown to directly interact with the cell membrane, resulting in significantly reduced shear sensitivity (Goldblum et al., 1990; Michaels et al., 1991).

The degree of protection though PLURONIC F-68 nonionic block copolymer depends on its concentration in the media. In many cases, 1 g/l is considered optimal in the literature (e.g. Mizrahi, 1984, Maiorella et al., 1988). In the case of IL-2SA, the concentration of PLURONIC F-68 nonionic block copolymer is also preferably 1 g/l (0.1%).

Structure and Nomenclature of PLURONIC Nonionic Block Copolymers

PLURONIC nonionic block copolymers generally comprise a hydrophobic polyoxypropylene (PPO) core block between hydrophilic polyoxyethylene (PEO) blocks, thus can be described generally as $PEO_m$-$PPO_n$-$PEO_m$ triblock molecules (see FIG. 1). The number of PEG blocks varies for different PLURONIC nonionic block copolymers from m=2-130, whereas the number of PPO blocks varies from n=15-67. The nomenclature of PLURONIC nonionic block copolymers as supplied by BASF Corp. of Parsippany N.J. includes a letter code for the physical form, i.e. either liquid (L), paste (P) or flake (F). The letter is followed by a 2 or 3 digit number. The first digit, or in case of a 3-digit-code, the first two digits, multiplied by 300 indicate the approximate molecular weight of the hydrophobic PPO part. The last digit multiplied by 10 gives the approximate content of hydrophilic PEG in the whole molecule (e.g. "8" stands for 80% PEG).

Physical Properties of PLURONIC F-68 nonionic block copolymer

PLURONIC F-68 nonionic block copolymer is a solid (flake) with 80% PEO content. The average molecular weight of the whole molecule is about 8.4 kD (BASF Corp., NJ).

Due to the high content of hydrophilic PEO (i.e., 80%), the molecule is more soluble than many other PLURONIC nonionic block copolymers (>100 g/l in water at 25° C.; manufacturer's information, BASF Corp, N.J.).

In contrast to conventional surfactants, the micellization of amphiphilic triblock copolymers is inherently more complex, and no sharp CMC (critical micelle concentration, the conc. at which micelles are formed for a given temperature) or CMT (critical micelle temperature, the temperature at which micelles are formed for a given concentration) is generally observed. Instead, a broad CMC and/or CMT range is found by light scattering and/or spectroscopic techniques, e.g. with fluorescence probes (Alexandridis and Hatton, 1995). This range is generally >100 g/L Since the formation of micelles is driven by entropy, and the free energy of micellization is mainly a function of the hydrophobic PPO block, PLURONIC F-68 nonionic block copolymer with its mainly hydrophilic character does not readily form micelles in water at RT (Alexandridis et al., 1994). Instead, for concentrations of 10 g/l in water, the CMT is around 45-50° C., whereas for concentrations of 100 g/l, the CMT is around 30-35° C. Therefore, for RT, the CMC is >100 g/l (Alexandridis et al., 1994).

PLURONIC F-68 nonionic block copolymer is known to cause some additional membrane fouling in the ultrafiltration step often employed for initial concentration/isolation. As discussed in Schulz et al. (1997) referenced supra, during ultrafiltration, a secondary membrane is formed, which properties dominate the retention of organic polymers. As a result, PLURONIC F-68 nonioinic block copolymer is at least partially retained even if high molecular weight cut-off membranes are used, which is only possible for particularly large products (e.g. 100 kD). PLURONIC F-68 nonionic block copolymer is therefore very difficult to remove by filtration processes (Schulz et al., 1997).

For example, data from a process for isolating a recombinant protein (IL-2SA) is provided. Detailed investigations have shown that PLURONIC F-68 nonionic block copolymer is co-concentrated during ultrafiltration processes and induces significant protein precipitation at concentration factors above 20-25 fold (for 1 g/l PLURONIC F-68 nonionic block copolymer in the media).

The methods of the present invention involve ultrafiltration, which may be accomplished using standard equipment and conditions known to those of skill in the art. The present invention also involves a step of adjusting the conductivity of a solution. This may be accomplished any way known to those of skill in the art. Particularly preferred is diafiltration, dilution, or gel filtration. Most preferred is diafiltration. As used herein, "solution" refers to a solution or suspension.

The invention is described in further detail by way of the following examples, which are included to amplify, but not limit the invention as described.

EXAMPLES

Example 1

Identification of Nature of Precipitate

Analysis of the precipitate formed during ultrafiltration concentration of cell culture supernatant by infrared spectroscopy clearly identifies protein as the main component of the precipitate.

Figure 3:
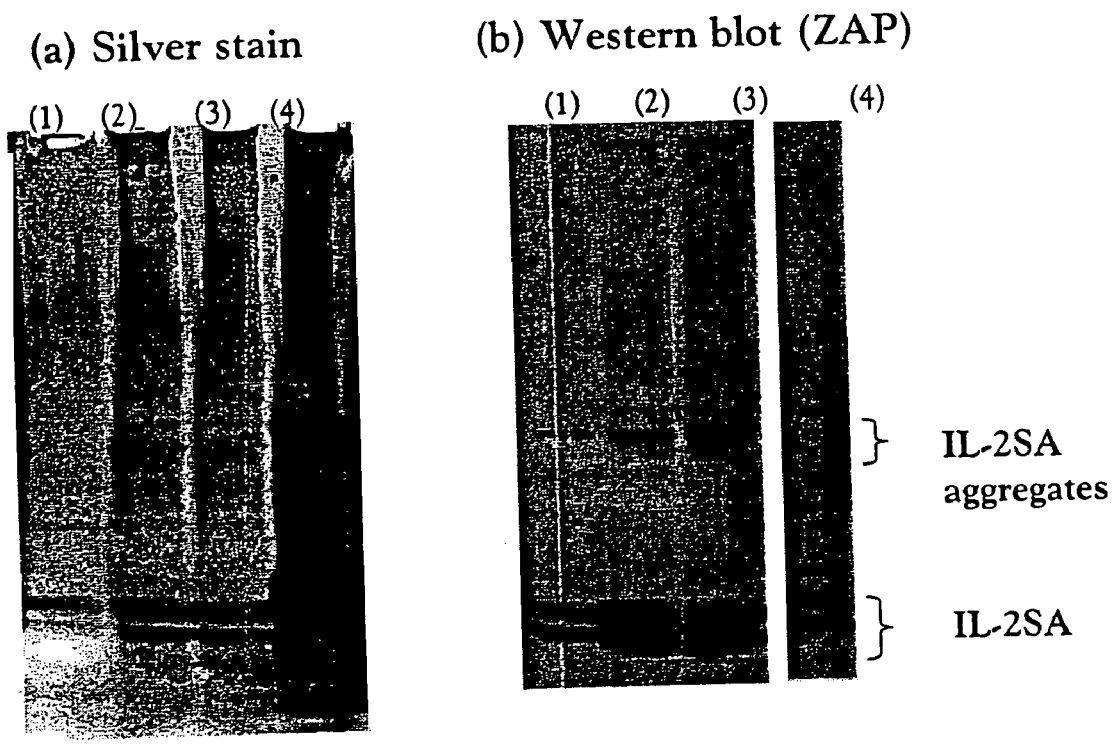
FIG. 3: (a) SDS gel electrophoresis followed by silver staining; (1)=IL-2SA standard (5 mg/l); (2)=UF concentrated harvest (25×); (3)=Supernatant of 25× after centrifugation; (4) Pellet re-dissolved in 1 ml buffer; (b) ZAP (western blot stained using anti-hIL-2-antibody); (1)=unconcentrated harvest; (2)=UF concentrated harvest (25×); (3)=Supernatant of 25× after centrifugation; (4) Pellet re-dissolved in 10 ml.

A 25 fold concentrated harvest from IL-2SA fermentation was obtained. The supernatant was subjected to centrifugation and the pellet re-dissolved in PBS. The UF concentrated harvest, supernatant of 25 fold concentration and redissolved pellet were analyzed by SDS gel electrophoresis followed by silver staining (see FIG. 3a) and immuno-staining (ZAP analysis) with an anti-hIL-2SA-antibody (see FIG. 3b). From FIG. 3a, (4) it can be seen that the precipitate, which was at least partially re-dissolved in buffer, indeed contains significant amounts of protein. As can be seen from FIG. 3b, (4) some IL-2SA also precipitates. However, the amount of precipitated IL-2SA seems to be relatively low (compare 3b, (4) and (3)), which is consistent with the rather reasonable yields of around 90% in conventional ultrafiltration process. Therefore, it can be concluded that mostly bulk protein (host cell protein) forms the precipitate encountered during ultrafiltration of cell culture supernatants.

Example 2

Co-Concentration of PLURONIC F-68 Nonionic Block Copolymer

The average molecular weight of PLURONIC F-68 nonionic block copolymer is 8.4 kD, which is relatively large. Due to the formation of secondary membranes during ultrafiltration processes and the inherently inhomogeneous conditions along the crossflow channel, the selectivity of conventional UF technology does usually not allow significant separation of molecules in the size range of PLURONIC nonionic block copolymer. Even for 100 kD UF membranes, as used for the largest protein products like rFVIII or gp220/350, significant retention and co-concentration of polymers like PLURONIC F-68 nonionic block copolymer is usually found (see e.g. Schulz et al., 1997). It can be assumed that the retention coefficient R of PLURONIC F-68 nanionic block copolymer during the ultrafiltration process with, e.g., a 10 kD NMWCO (nominal molecular weight cut-off) will be close to 1 (or 100%). Since the PLURONIC F-68 nonionic block copolymer concentration in the medium required to obtain adequate cell protection during fermentation is 1 g/l (0.1%), 30 fold concentration would therefore lead to up to 30 g/l (or 3%) PLURONIC F-68 nonionic block copolymer in the UF concentrate.

To confirm this hypothesis, retentate samples of various concentration factors (1×=culture supernatant, 2×, 4×, 8×, 16× and approx. 50×) were submitted for analysis by Thin Layer Chromatography (TLC). The resulting PLURONIC F-68 nonionic block copolymer concentrations were estimated as 1-2 g/l for 1 and 2×, 4 g/l for 4×, 4-10 g/l for 8×, 10 g/l for 16× and 50 g/l for 50×. Considering the inherent inaccuracy of the TLC method, these results clearly confirm the almost complete co-concentration of PLURONIC F-68 nonionic block copolymer.

Figure 4:
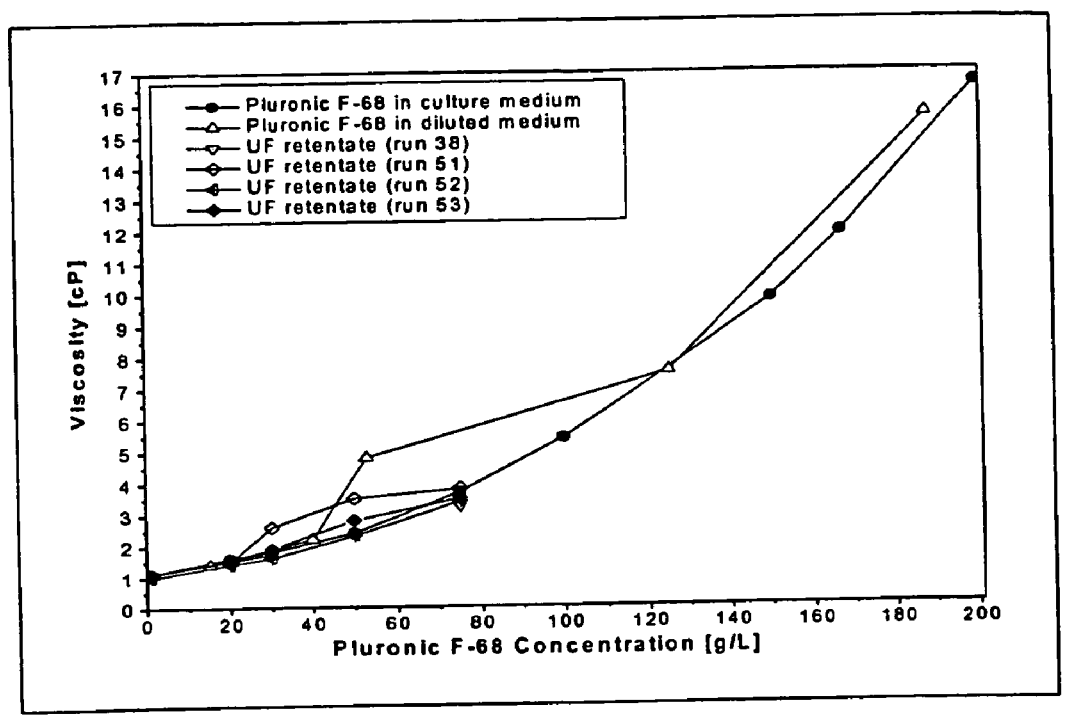
FIG. 4: Viscosity of PLURONIC F-68 nonionic block copolymer solutions prepared in cell culture medium and various ultrafiltration concentrates. Dilution of culture medium was performed with WFI to reach 1-1.5 mS/cm conductivity.

This co-concentration of PLURONIC F-68 nonionic block copolymer has of course the additional effect of increasing the viscosity of the product solution. As can be seen from FIG. 4, concentrates from several UF runs show indeed similar viscosity profiles (as a function of the assumed PLURONIC F-68 nonionic block copolymer concentration) as PLURONIC F-68 nonionic block copolymer solutions of known concentration prepared in either culture media or diluted culture media.

Example 3

Spiking Experiments with PLURONIC F-68 Nonionic Block Copolymer

Figure 5:
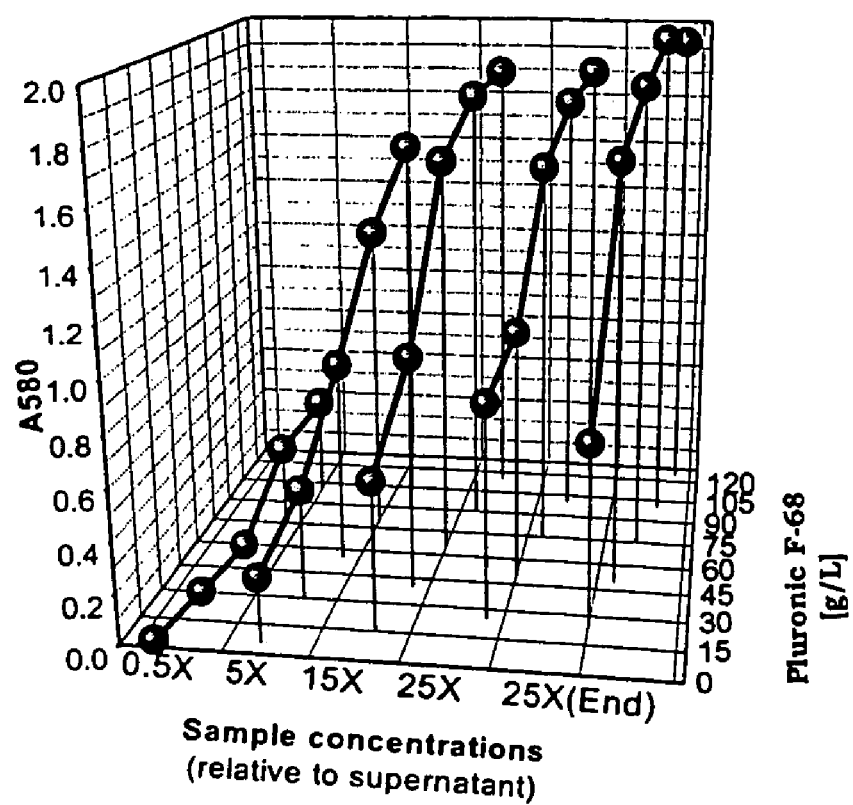
FIG. 5: Precipitation during spiking of PLURONIC F-68 nonionic block copolymer into ultrafiltered culture harvest of different concentration as measured by increase in absorbance at 580 um in a standard cuvette in a standard spectrophotometer (compare also FIG. 2). Material for 25× (End)-sample taken from final drained concentrate.
Figure 6:
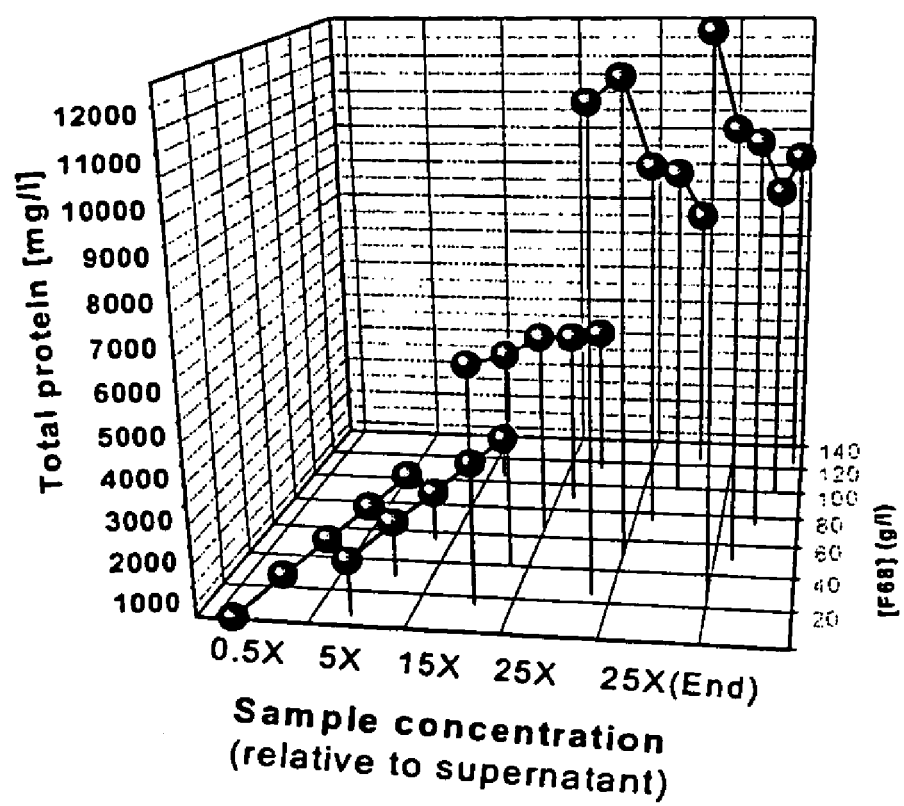
FIG. 6: Remaining total protein after centrifugation for PLURONIC F-68 nonionic block copolymer spiking experiments (compare also FIG. 2). Material for 25× (End)-sample taken from final drained concentrate.
Figure 7:
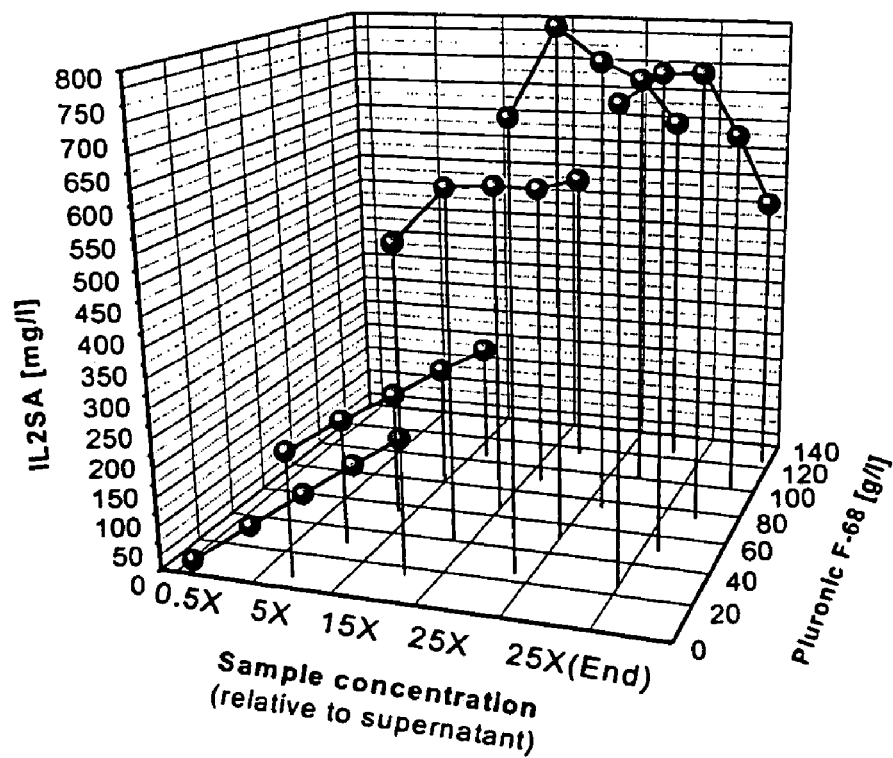
FIG. 7: Remaining IL-2SA in solution after centrifugation for PLURONIC F-68 nonionic block copolymer spiking experiments (compare also FIG. 2). Material for 25× (End)-sample taken from final drained concentrate.

Since it has been demonstrated that the end concentration of PLURONIC F-68 nonionic block copolymer in ultrafiltration retentate is usually very high, spiking experiments with culture supernatant and concentrates of different concentration factors were performed in order to characterize the influence of these higher PLURONIC F-68 nonionic block copolymer concentrations on protein solubility. As can be seen from FIG. 5, spiking PLURONIC F-68 nonionic block copolymer into samples of pre-concentrated culture supernatant indeed causes strong precipitation. As expected, the PLURONIC F-68 nonionic block copolymer induced precipitation appears to be more severe for a higher concentration factor. FIG. 6 shows the remaining total protein in solution as measured by the Bradford assay (after centrifugation) as a function of concentration factor and PLURONIC F-68 nonionic block copolymer concentration. These results are consistent with the A580 measurements and confirm that the protein is precipitating out as a function of the added PLURONIC F-65 nonionic block copolymer concentration and the overall concentration factor. As can be seen from FIG. 7, this is in principle true also for the example of the IL-28A product molecule.

This induction of protein precipitation by increased PLURONIC F-68 nonionic block copolymer concentrations is believed to be caused by two effects. First, the binding of water molecules to the hydrophilic PEO blocks of the PLURONIC F-68 nonionic block copolymer reduces availability of water molecules for the hydration hull of proteins. Second, the increased PLURONIC F-68 nonionic block copolymer concentration decreases the dielectric constant of the medium, which enhances Coulomb interactions between protein molecules. The overall result is a reduction of the electrostatic shielding and therefore a decrease of the capacity of the system to fully solvate the proteins molecules.

Figure 8:
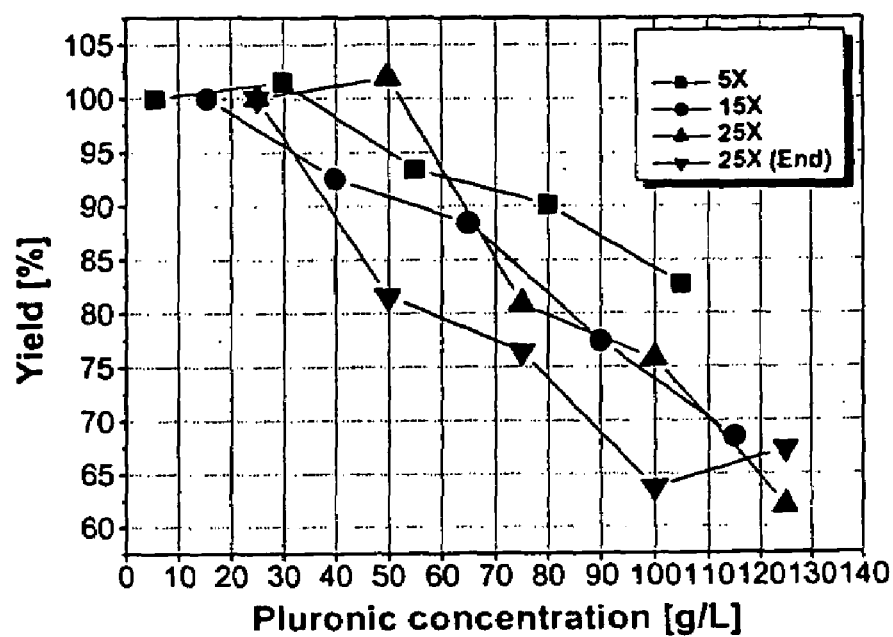
FIG. 8: Bulk protein yield after PLURONIC F-68 nonionic block copolymer-induced precipitation. Shown are curves for various protein concentrations (compare FIG. 2). Material for 25× (End)-sample taken from final drained concentrate.

Protein starts to precipitate at PLURONIC F-68 nonionic block copolymer concentrations of around 20-30 g/l (see FIG. 8). This is consistent with the fact that in conventional process, severe precipitation starts to occur around 20-25 fold concentration, since at 1 g/l starting concentration of PLURONIC F-68 nonionic block copolymer in the medium and 100% retention, end concentrations will be 20-25 g/l.

Figure 9:
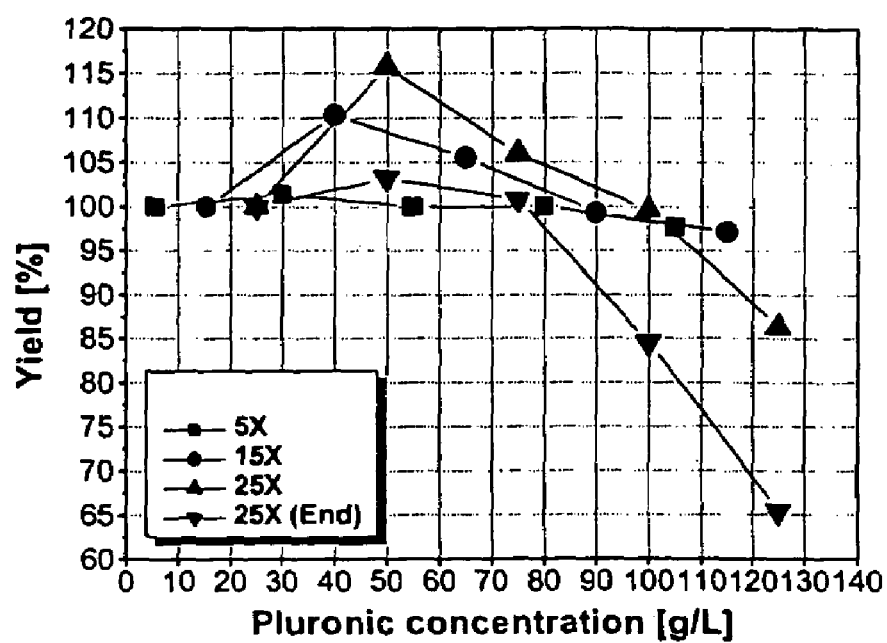
FIG. 9: IL-2SA yields after F-68 nonionic block copolymer-induced precipitation. Shown are curves for various protein concentrations (compare FIG. 2). Material for 25× (End)-sample taken from final drained concentrate.

For the example of IL-2SA, the product molecule precipitates at somewhat higher PLURONIC F-68 nonionic block copolymer concentrations (see FIG. 9), which explains that the conventional process still had relatively reasonable yields in the UF process itself although high losses occurred in the subsequent steps as a result of the precipitation.

Comparative Example 4

Hydrodynamic Strategy to Minimize Protein Precipitation

To minimize protein precipitation, the maximum protein concentration in the system should be minimized. Due to the convective transport of retained solutes towards the membrane surface, the maximum protein concentration in any given crossflow ultrafiltration system is reached in the laminar boundary layer at the membrane surface, i.e. it equals $c_{wall}$. From a simple mass balance it follows that the wall concentration depends exponentially on the permeate flux J and the mass transfer coefficient $k_D$ (see FIG. 10):

$$\frac{c_{wall}}{c_{bulk}} = e^{\left(\frac{J}{k_d}\right)}$$

Figure 10:
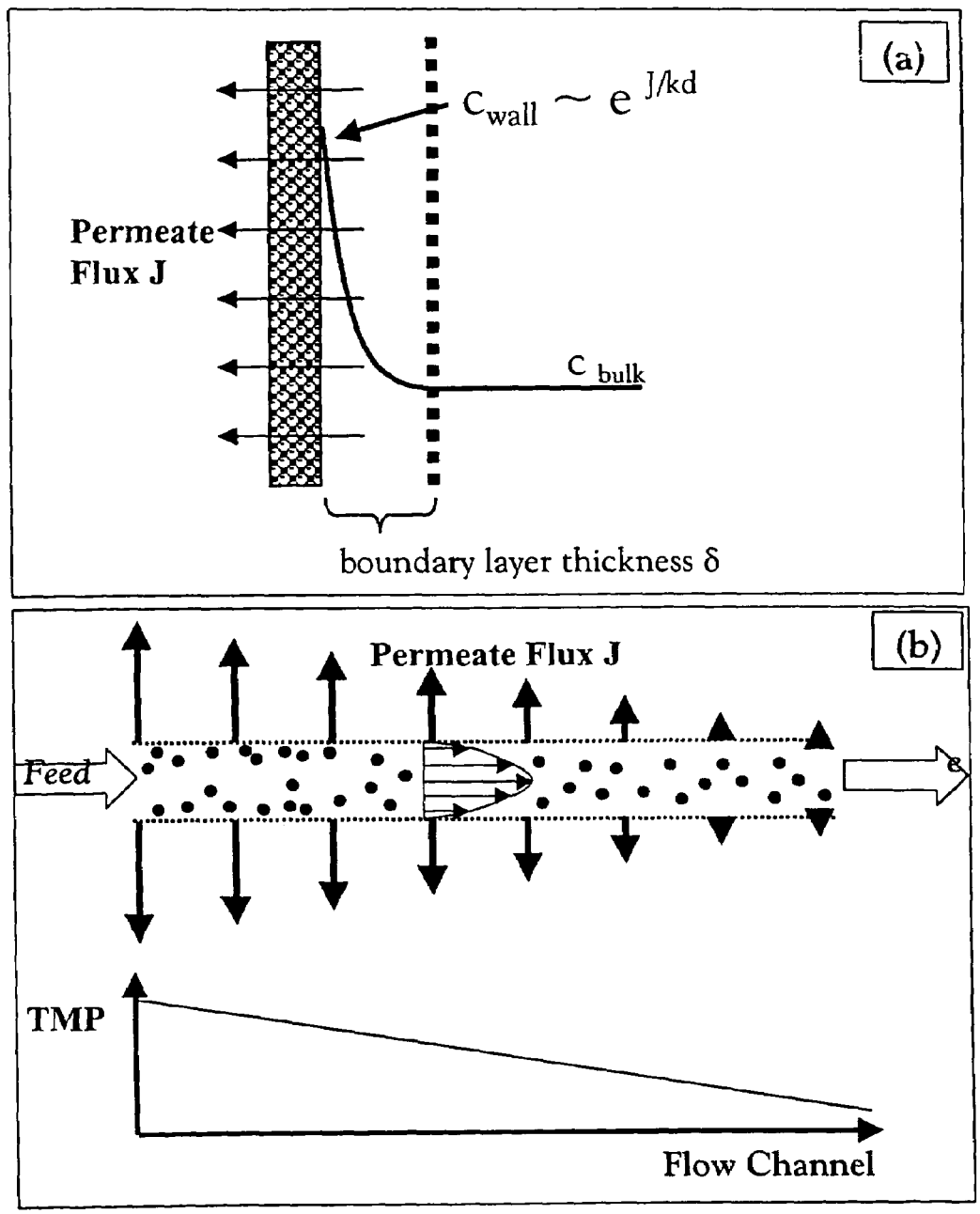
FIG. 10: (a) Concentration profile for retained solutes at membrane surface (schematic), (b) Inhomogeneous pressure distribution and consequently inhomogeneous permeate flux in crossflow filtration (from Vogel et al., 2002), "TMP" is transmembrane pressure.

Mass Balance for Complete Retention (R=1; compare FIG. 10)

For the case of turbulent flow in the spacer-filled flow channel and laminar boundary layer at the membrane surface (film model), the following mass balance applies:

(accumulation of protein mass at membrane)=(convective transport)−(diffusive backtransport)

$$\frac{dm_{wall}}{dt} = \frac{dm}{dt} - D \cdot A \cdot \frac{dc}{dy} \text{ (employing Fick's law for diffusional transport)}$$

with $dm/dt = c * F$ ($F$ = volumetric flow through membrane[e.g liters/h])

$$\frac{dm_{wall}}{dt} = c \cdot F - D \cdot A \cdot \frac{dc}{dy}$$

in steady state, the protein accumulation at the surface is =0; separation of variables leads to:

$$-\frac{1}{c} \cdot dc = \frac{F}{A} \cdot \frac{1}{D} \cdot dy$$

integration from y=0 (c=$c_{wall}$) to y=boundary layer thickness δ (c=$c_{bulk}$):

$$\int_{c_{wall}}^{c_{bulk}} -\frac{1}{c} dc = \int_0^\delta J \cdot \frac{1}{D} d$$

leads to:

$$\ln\left(\frac{c_{wall}}{c_{bulk}}\right) = J \cdot \frac{\delta}{D}$$

and thus to the specific flux (complete retention):

$$J = \frac{D}{\delta} \cdot \ln\left(\frac{c_{wall}}{c_{bulk}}\right)$$

Consequently, the normalized surface concentration for any adjusted filtrate flux J is:

$$\frac{c_{wall}}{c_{bulk}} = e^{\left(\frac{J}{k_d}\right)}$$

Symbol List
A area
C concentration
$c^{eq}$ concentration at equilibrium
D diffusion coefficient
δ thickness of laminar boundary layer
F volumetric flow
J permeate flux
$k_D$ mass transfer coefficient
M mass
$q^{eq}$ bound mass per unit of resin in equilibrium The mass transfer coefficient (which can be estimated based on empirical or semi-empirical correlation of Sherwood number with Reynolds- and Schmidt-number) depends on the crossflow velocity in the system and its geometry. However, the mass transfer is difficult to optimize in conventional crossflow systems because of the inherent coupling of shear force and pressure generation (See, i.e., Vogel, J. H.: "Kontrollierte Scheraffinitätsfiltration: Eine neue Technik zur integrierten Aufarbeitung pharmazeutischer Proteine aus tierischer Zellkultur." Fortschr.-Ber. VDI Reihe 17, Nr. 185. VDI Verlag, Duesseldorf. ISBN 3-18-318517-2. ISSN 0178-9600. 1999, Vogel, J. H., Anspach, B., Kroner, K.-H, Piret, J. M., Haynes, C. A.: Controlled Shear Affinity Filtration (CSAF): A New Technology for Integration of Cell Separation and Protein Isolation from Mammalian Cell Cultures. Biotechnology and Bioengineering. Vol. 78, 7. p 806-814. 2002, both of which are incorporated herein by reference.). More specifically, increasing the crossflow velocity in order to increase $k_D$ also increases the pressure drop in the flow channel. This in turn creates inhomogeneous conditions in which $c_{wall}$ can vary along the flow channel.

In any case, it has been shown that the hydrodynamic approach to reduce $c_{wall}$ can only slightly reduce overall protein precipitation induced by PLURONIC nonionic block copolymer, thus allowing only marginally higher concentration factors to be achieved without additional yield losses. Therefore, there was a need for a fundamentally new solution, and this problem has been successfully addressed by processes and products according to the present invention.

Example 5

Figure 11:
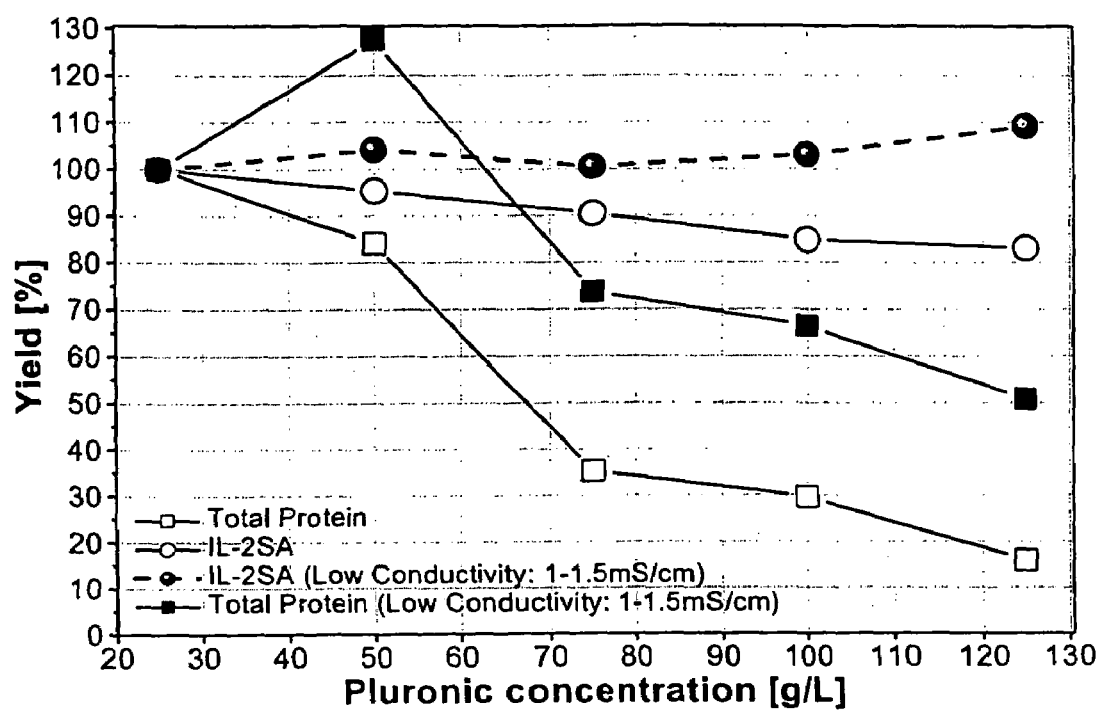
FIG. 11: PLURONIC nonionic block copolymer-induced precipitation of total protein and IL-2SA and its reduction by lowered conductivity (spiking experiments). Low conductivity=1–1.5 mS/cm.

The Influence of Conductivity on PLURONIC Nonionic Block Copolymer-Induced Protein Precipitation Under the physiological conditions of cell culture medium and harvest, protein solubility is usually good. However, it was speculated that for the concentrated cell culture supernatant, the high PLURONIC Nonionic Block Copolymer concentrations will draw more water away from the hydration hulls of proteins, most likely allowing for thermodynamically driven hydrophobic interactions between proteins and eventually resulting in protein precipitation. In effect, this situation might be characterized by "increased competition" for water molecules required to maintain protein solubility. Since PLURONIC Nonionic Block Copolymer cannot be effectively separated, it was tested by further spiking experiments if a reduction in salt content by diafiltration against WFI (water for injection) helps to maintain protein solubility. As can be seen from FIG. 11, by reducing conductivity from 11-12 mS/cm (as in harvest) to about 1-1.5 mS/cm, proteins appear to precipitate only at high PLURONIC F-68 nonionic block copolymer concentration.

Figure 12:
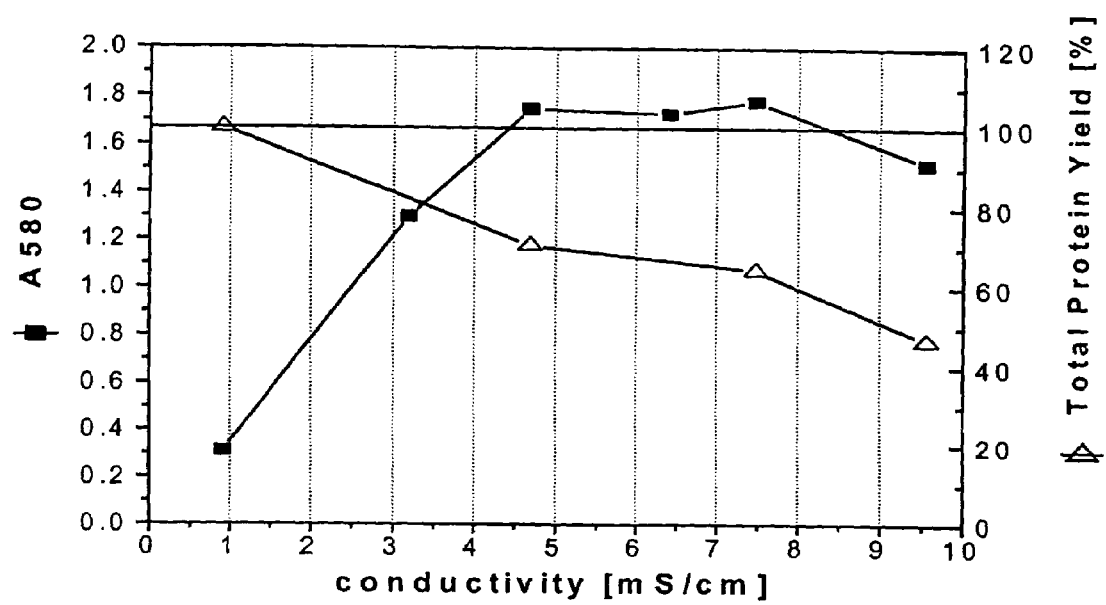
FIG. 12: Influence of salt addition to diafiltered low conductivity concentrate on precipitation of bulk protein.

In order to confirm the influence of conductivity, salt was added to low conductivity samples to restore the original conductivity of cell culture supernatant (see FIG. 12). NaCl (1M stock solution) was added stepwise under mixing to diafiltered 50× concentrate (approximately 0.9 mS/cm, pH 7.14) to increase conductivity. The increase in A580 absorption and decrease in soluble protein show that adding back salt reverses the effect of lowered conductivity. In this case, strong protein precipitation is induced, as measured by A580 (see FIG. 12).

These results demonstrate that lowering the concentrations of salts can significantly reduce or even eliminate product precipitation.

Example 6

The Influence of pH on Precipitation

Figure 13:
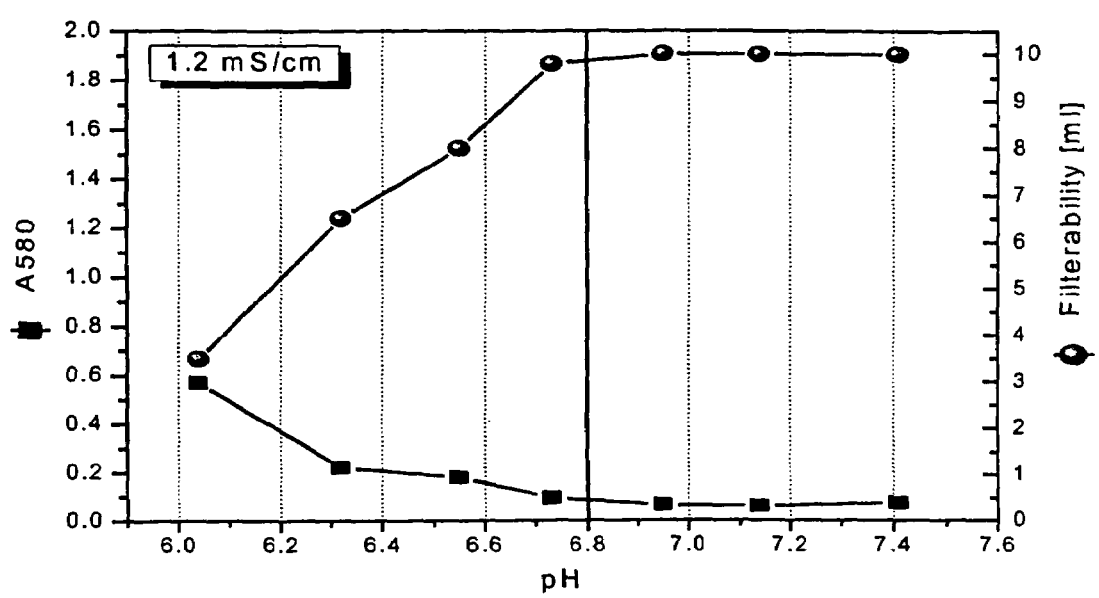
FIG. 13: Influence of pH on precipitation. Concentrated phosphoric acid was used for stepwise decrease of pH of UF/DF/UF 75× concentrate.
Figure 14:
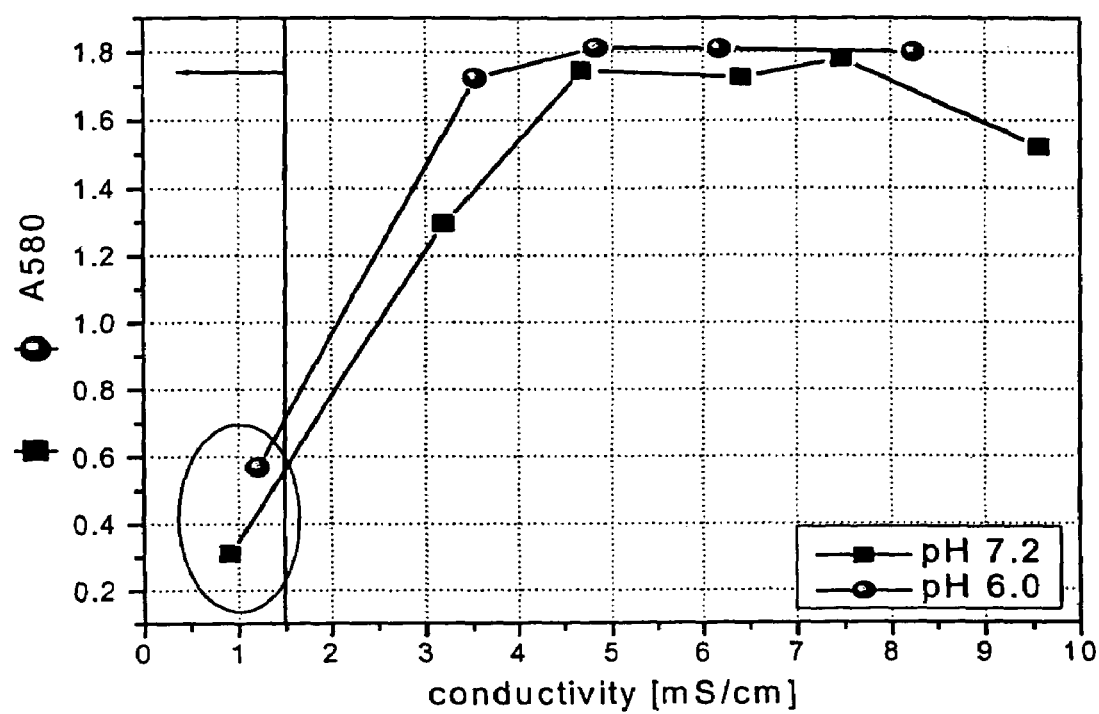
FIG. 14: Influence of conductivity on precipitation for two different ph (pH 6.0 adjusted by addition of concentrated phosphoric acid). UF/DF/UF 75× concentrate was used in both cases.

From FIG. 13 it can be seen that at low conductivity (i.e. from 0.5 to 5, particularly 1.2 mS/cm), precipitation is efficiently avoided. Such conditions can be achieved for example by maintaining a pH of greater than 6.7. If the pH is reduced below about 6.7, A580 increases indicating precipitation, while the filterability of the material starts to drop. It should be noted that the pH of cell culture fermentations is controlled around neutral conditions, which apparently is within the range of minimized precipitation. A potential decrease of pH during storage is negligible since metabolic activity of any remaining viable cells in stored harvest is low at 4° C. storage temperature. On the contrary, since the buffer system of the cell culture medium is often bicarbonate based, outgassing of $CO_2$ (e.g. during UF) leads to a further slight increase the pH. In any case, for reasonably high pH values, the sensitivity of precipitation with regard to conductivity is higher then the sensitivity with regard to pH (see FIG. 14).

Example 7

A Preferred Isolation Scheme of the Invention

UF/DF/UF

Figure 15:
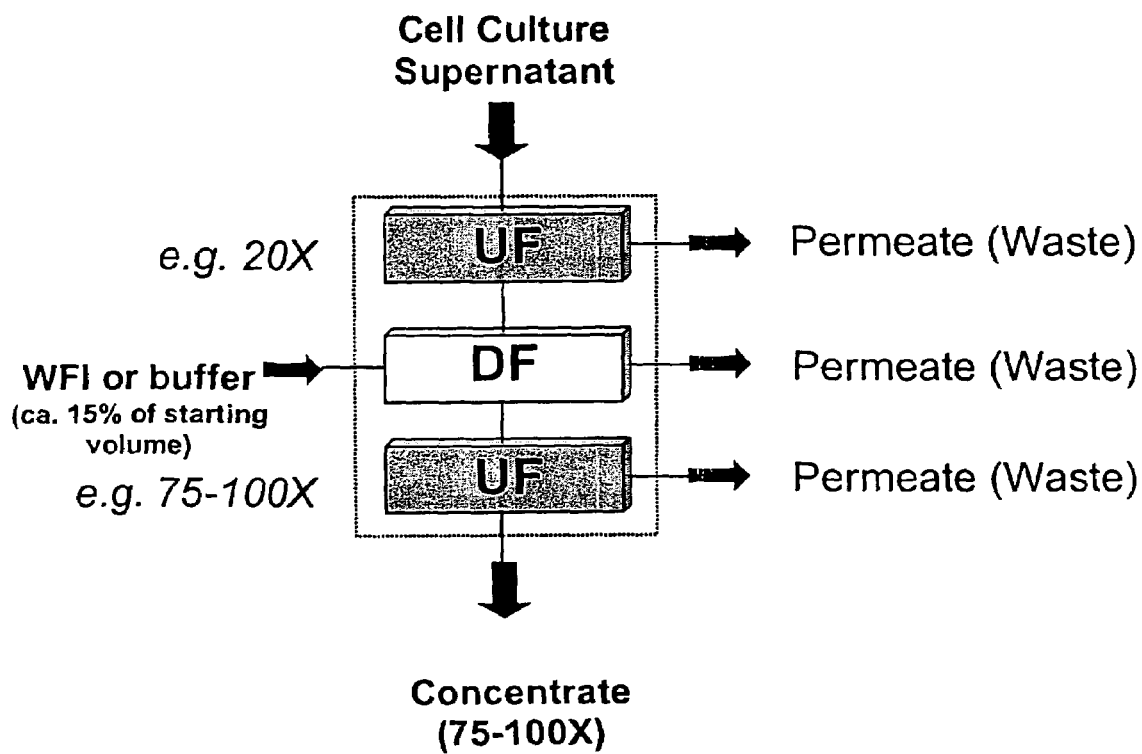
FIG. 15: The UF/DF/UF isolation process scheme according to a preferred embodiment of the invention.

A preferred method of the invention comprises ultrafiltration, diafiltration, then ultrafiltration ("UF/DF/UF") (compare FIG. 15). In a first step, the cell culture supernatant is concentrated by ultrafiltration to a concentration factor known not to cause product loss, such as 20×. Then, in the same UF equipment, the concentrate is diafiltered against water (WFI) or buffer to lower the conductivity to the point where PLURONIC nonionic block copolymer-induced product precipitation is efficiently prevented. Finally, the material is further concentrated to achieve very high final concentration factors (e.g. 75-100×) without product loss and with minimized bulk protein precipitation. The initial concentration is intended to minimize water/buffer consumption and overall process time. By using this step, the required volume for subsequent diafiltration is only approximately 15% of the starting volume of cell culture supernatant. After diafiltration, concentration is resumed to reach very high final concentration factors (e.g. >75-100 fold). Due to the lowered ionic strength, the proteins remain in solution and filterability remains high.

All three steps can be performed in the same equipment if desired. In this case, there is no increase in complexity and no new material or hardware qualification is necessary. The initial UF step allows minimization of WFI consumption. Since the additional volume that has to be filtered during the DF step is therefore low (usually less than 15% more), the overall process time is not significantly prolonged.

Figure 16:
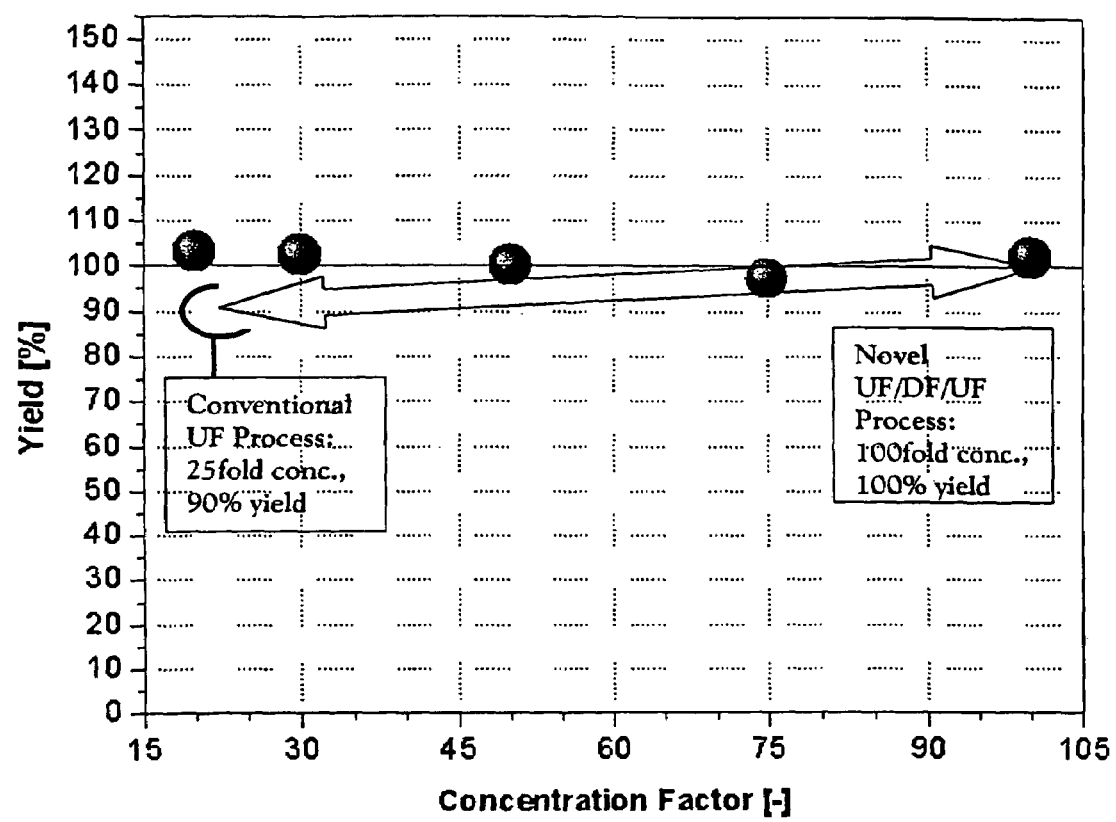
FIG. 16: Performance of the UF/DF/UF isolation process scheme of the invention in comparison to conventional UF process.
Figure 17:
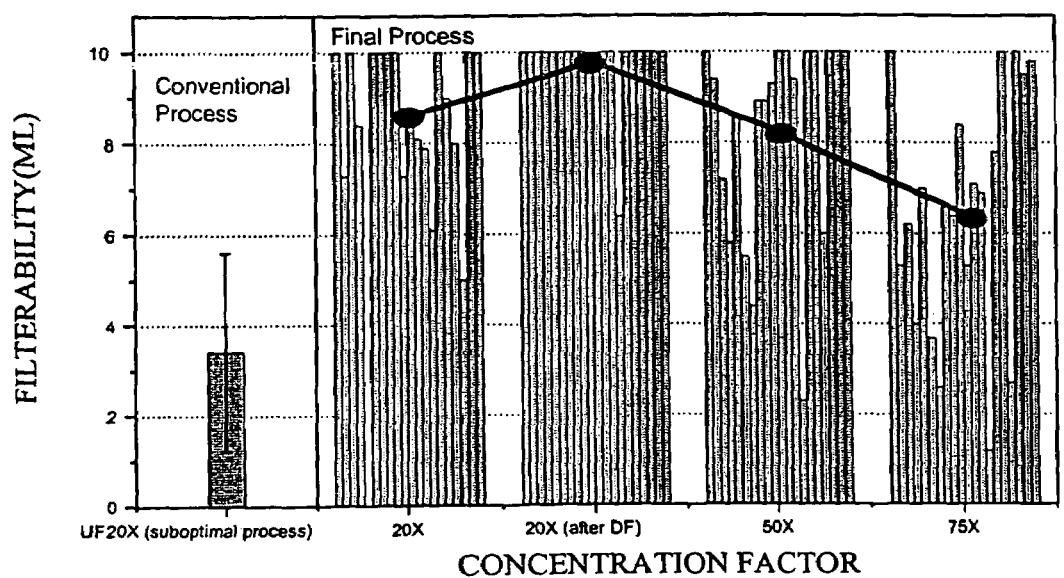
FIG. 17: Filterability of concentrated IL-28A bulk generated by the new UF/DF/UF isolation process scheme in comparison to conventional UF/DF process.

For the example of IL-2SA, FIG. 16 shows the yield a process according to the present invention measured at different stages from 20× up to 100× final concentration factor. As can be seen, the new process allows for a significant increase in concentration factor, while simultaneously maximizing product yield compared to a conventional process. Concentration factors are increased up to 5 fold and yield is maximized. Precipitation is significantly reduced, as can be seen from the filterability data shown in FIG. 17.

Example 8

Figure 18:
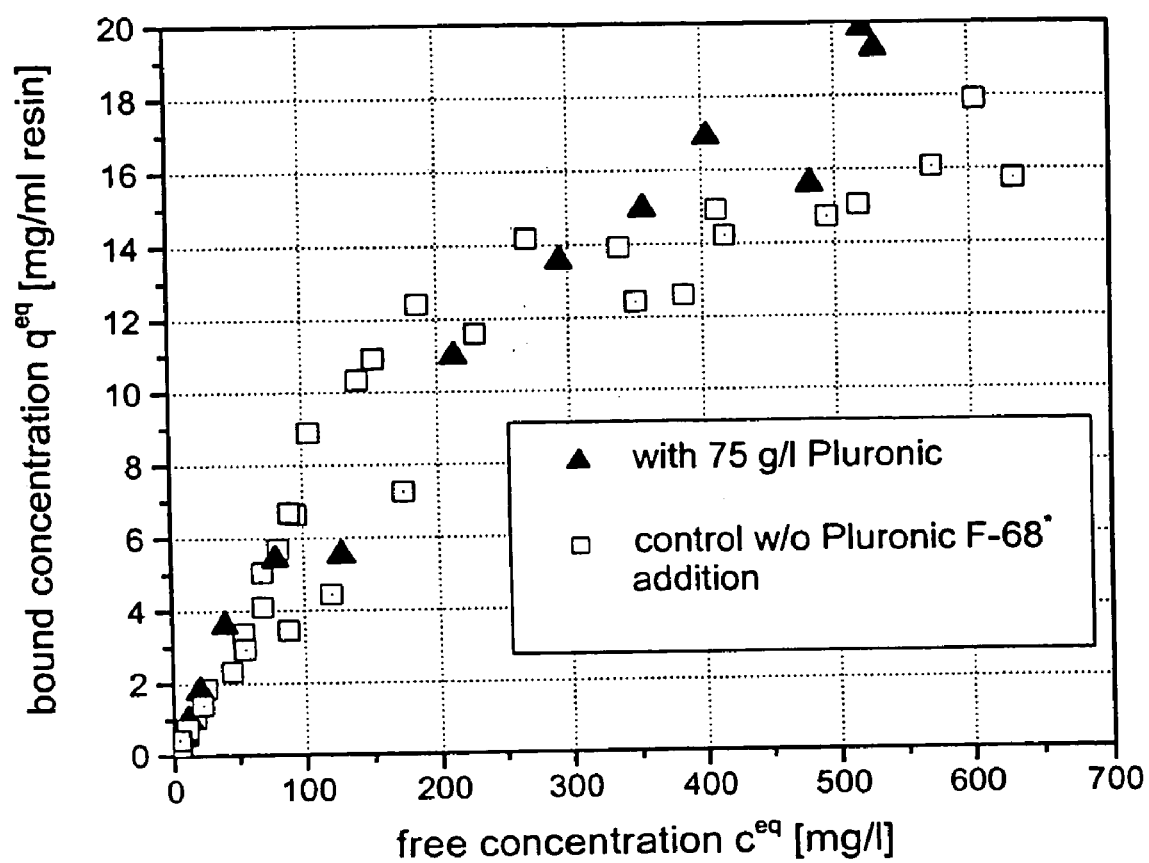
FIG. 18: Influence of high PLURONIC F-68 nonionic block copolymer concentrations (75 g/l) on binding of IL-2SA to the cation exchange resin SP Sepharose FF (Amersham Pharmacia Biotech).

Influence of High PLURONIC Nonionic Block Copolymer Concentrations on Downstream Processing/Cation Exchange Chromatography A higher concentration factor achieved by the UF-DF-UF process means that the PLURONIC F-68 nonionic block copolymer concentration of the material going into the first purification column will be higher as well, e.g. approx. 75 g/l (or 7.5%) for a 75× target value. Therefore, further studies were performed to evaluate if these high PLURONIC nonionic block copolymer concentrations might have a negative impact on the initial downstream purification step. Often the first purification step is a cation exchange chromatography. FIG. 18 shows adsorption isotherms for a standard ion exchange resin at 20° C. with and without additional spiked PLURONIC F-68 nonionic block copolymer. Since PLURONIC F-68 nonionic block copolymer is an essential media component, no completely PLURONIC nonionic block copolymer-free concentrate was available. However, the UF-DF-UF-TCF 75 fold concentrate was diluted up to 160 fold for the measurement of The "control" isotherm, yielding very low PLURONIC F-68 nonionic block copolymer concentrations, especially for the initial slope of the isotherm. In contrast, dilution with a 75 g/l PLURONIC F-68 nonionic block copolymer solution in pre-diluted media yields 75 g/l PLURONIC F-68 nonionic block copolymer end concentration for all points of the isotherm. As can be seen from the figure, both isotherms are very similar, indicating no negative effect of the raised PLURONIC nonionic block copolymer-levels on adsorption thermodynamics.

PLURONIC nonionic block copolymer will be co-concentrated in practically all ultrafiltration processes. As a result, it induces protein precipitation, which usually will start at about 20-25 fold concentration factor. This "universal" protein precipitation problem leads to yield losses and other problems in the isolation/purification process and prevents the achievement of higher concentration factors.

Using IL-2SA as a model example, it has been demonstrated that reducing the ionic strength of the culture supernatant can efficiently prevent or minimize PLURONIC nonionic block copolymer-induced protein precipitation up to very high PLURONIC nonionic blocks copolymer concentrations.

The resulting new isolation scheme (UF/DF/UF) offers an efficient and robust solution to the precipitation problem. It allows the achievement of up to 100 fold concentration (i.e. up to 5 fold higher then in the old process), with maximized yield and improved filterability. This in turn dramatically further downstream operations Furthermore, it has been shown that the resulting high PLURONIC F-68 nonionic block copolymer concentrations (up to 75 g/l and higher) do not have a negative influence on IL-2SA binding during downstream cation exchange.

Therefore, the UF/DF/UF process scheme appeals as a very suitable "platform technology" for the isolation of proteins from cell culture fermentation. Besides its increased performance, it is robust and easy to implement and utilizes the same standard ultrafiltration equipment and cleaning procedures as conventional UF.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined herein and equivalents.

The following documents have been published that relate generally to the recovery of proteins produced from mammalian and insect cell cultures using ultrafiltration as well as to certain materials such as polymers used in connection therewith:

Alexandridis, P. and Hatton, T. A.: Poly(ethylene oxide)-poly (propylene oxide)-poly(ethylene oxide) block copolymer surfactants in aqueous solutions and at interfaces: thermodynamics, structure, dynamics, and modeling. Colloids and Surfaces A: Physicochemical and Engineering Aspects 96. 146. 1995.

Alexandridis, P., Holzwarth, J. F. and Harton, T. A. Macromolecules. 27, 2414. 1994.

Augenstein, D. C., Sinskey, A. J. and Wang, D. I. C.: Effect of shear on the death of two strains of mammalian tissue cells. Biotechnol. Bioeng. 13, 409-418. 1971.

Bavarian, F., Chalmers, J. J.: Microscopic visualization of insect cell-bubble interactions. II: The bubble film and bubble rupture. Biotechnol. Prog. 7, 2, 151-58. 1991.

Boulton-Stone, J. M. and Blake, J. R.: Gas-bubbles bursting at a free surface. J. Fluid Mech. 154. 437-466. 1993.

Garcia-Briones, M. A. and Chalmers, J. J.: Cell-bubble interactions: Mechanisms of suspended cell damage. Ann. N.Y. Acad. Sci. 655, 219-229. 1992.

Garcia-Briones, M. A., Brodkey, R. S. and Chalmers, J. J.: Computer simulations of the rupture of a gas bubble at a gas-liquid interface and its implications in animal cell damage. Chem. Eng. Sci. 49. 2301-2320. 1994.

Goldblum, S., Bae, Y., Hink, W. F. and Chalmers, J. J.: Protective effect of methylcellulose and other polymers on insect cells subjected to laminar shear stress. Biotechnol. Prog. 6. 383-390. 1991.

Jordan, M., Sucker, H., Binsele, A., Widmer, F., Eppenberger, H, M.: Interactions between animal cells and gas bubbles: the influence of serum and PLURONIC F-68 on the physical properties of the bubble surface. Biotechnol. Bioeng. Vol. 43. 1994.

Maiorella, B., Inlow, D., Shauger, A., Harano, D.: Large-Scale Insect Cell-Culture for Recombinant Protein Production. Bio/technol. 6. 1406-1410. 1988.

Michaels, J. D., Peterson, J. F., McIntire, L. V., Papoutsakis, B. T: Protection mechanism of freely suspended animal cells (CRL 8018) from fluid-mechanical injury. Viscometric and bioreactor studies using serum, PLURONIC F-68 and polyethylene glycol. Biotechnol. Bioeng. 38. 169-180. 1991.

Michaels, J. D., Nowak, J. E., Malik, A. K., Koczo, K., Wason, D. T., Papoutsakis, E. T.: Analysis of cell-to-bubble attachment in sparged bioreactors in the presence of cell-protecting additives. Biotechnol. Bioeng. 47. 420-430. 1995a.

Michaels, J. D., Nowak, J. E., Malik, A. K., Koczo, K., Wason, D. T., Papoutsakis, E. T.: Interfacial properties of cell culture media with cell-protecting additives. Biotechnol. Bioeng. 47. 407-419. 1995b.

Mizrahi, A.: Oxygen in human lymphoblastoid cell line cultures and effect of polymers in agitated and aerated cultures. Develop. Biol. Standard 55, 93-102. 1984.

Murhammer, D. W., Goochee, C. F.: Scale-up of insect cell cultures: protective effects of PLURONIC F-68. Biotechnology. Vol. 6. 1988.

Murhammer, D. W., Goochee, C. F.: Structural features of non-ionic polyglycol polymer molecules responsible for the protective effect in sparged animal cell bioreactors. Biotechnology Progress. 1990.

Schurch, U., Kramer, H., Einsele, A., Widmer, F. and Eppenberger, H. M.: Experimental evaluation of laminar shear stress on the behaviour of hybridoma mass cell cultures producing antibodies against mitochondrial creatinine jinase. J. Biotechnol. 7, 179-191. 1988.

Schulz, C., Vogel, J. H., Scharfenberg, K.: Influence of PLURONIC F-68 on the Ultrafiltration of Cell Culture Supernatants in: Carrondo et al. (eds). Animal Cell Technology, From Vaccines to Genetic Medicine, Kluwer Academic Publishers. 1997.

Vogel, J. H.: "Kontrollierte Scheraffinitätsfiltration: Eine neue Technik zur integrierten Aufarbeitung pharmazeutischer Proteine aus tierischer Zellkultur." Fortschr.-Ber. VDI Reihe 17, Nr. 185. VDI Verlag, Duesseldorf. ISBN 3-18-318517-2. ISSN 0178-9600. 1999.

Vogel, J. H., Anspach, B., Kroner, K.-H, Piret, J. M., Haynes, C. A.: Controlled Shear Affinity Filtration (CSAF): A New Technology for Integration of Cell Separation and Protein Isolation from Mammalian Cell Cultures. Biotechnology and Bioengineering, Vol. 78, 7, p 806-814. 2002.

The invention claimed is:

1. A method for concentrating a macromolecule from an aqueous starting solution having solution components, the solution components comprising the macromolecule and an organic polymer, the method comprising: (1) subjecting the aqueous starting solution to ultrafiltration to concentrate the macromolecule such that a first retentate solution is produced, (2) adjusting the conductivity of the first retentate solution such that precipitation of the solution components induced by the organic polymer is substantially prevented or substantially reversed without removal of the organic polymer to produce a second retentate solution, and (3) subjecting the second retentate solution to ultrafiltration to further concentrate the macromolecule such that a concentrated solution having at least a 50-fold higher concentration of the macromolecule than the aqueous starting solution is produced.

2. The method of claim 1 wherein the conductivity is adjusted by diafiltration against water, suitable diluent or buffer.

3. The method of claim 1 wherein the conductivity of the first retentate solution is adjusted to below about 6 mS/cm as measured at 22° C.

4. The method of claim 3 wherein the conductivity of the first retentate solution is adjusted to between about 0.5 to 5 mS/cm as measured at 22° C.

5. The method of claim 1 wherein the conductivity of the first retentate solution is adjusted to between about 1.0 and 1.5 mS/cm as measured at 22° C.

6. The method of claim 1 wherein the organic polymer is a nonionic block copolymer.

7. The method of claim 1 wherein the organic polymer is a solid (flake) polyoxyethylene-polyoxypropylene block copolymer with 80% polyoxyethylene content and an average molecular weight of about 8.4 $k_D$.

8. The method of claim 1 wherein the macromolecule is a protein.

9. The method of claim 1 wherein the starting solution comprises mammalian or insect cell culture supernatant.

10. The method of claim 1 wherein the concentrated solution has at least a 100 fold higher concentration of the macromolecule than the starting solution.

11. The method of claim 1 wherein the organic polymer is selected from the group consisting of polyoxyethylene-polyoxypropylene-polyoxyethylene triblock copolymers, polyethylene glycol, and antifoam polymers.

* * * * *

UNITED STATES PATENT AND TRADEMARK OFFICE
CERTIFICATE OF CORRECTION

| | | |
|---|---|---|
| PATENT NO. | : 7,674,885 B2 | Page 1 of 1 |
| APPLICATION NO. | : 10/532998 | |
| DATED | : March 9, 2010 | |
| INVENTOR(S) | : Konstantin Konstantinov et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 809 days.

Signed and Sealed this

Fourth Day of January, 2011

David J. Kappos
*Director of the United States Patent and Trademark Office*